(12) United States Patent  
Torlei et al.

(10) Patent No.: US 10,327,941 B2
(45) Date of Patent: Jun. 25, 2019

(54) CERVICAL NECK BRACE

(71) Applicant: THE ROYAL UNITED HOSPITALS BATH NHS FOUNDATION TRUST, Bath (GB)

(72) Inventors: Karina Torlei, London (GB); Michael Hillman, Bristol (GB); Jonathan Benger, Bristol (GB)

(73) Assignee: THE ROYAL UNITED HOSPITALS BATH NHS FOUNDATION TRUST, Bath (GB)

( * ) Notice: Subject to any disclaimer, the term of this patent is extended or adjusted under 35 U.S.C. 154(b) by 427 days.

(21) Appl. No.: 14/425,045

(22) PCT Filed: Aug. 29, 2013

(86) PCT No.: PCT/GB2013/052277
§ 371 (c)(1),
(2) Date: Mar. 1, 2015

(87) PCT Pub. No.: WO2014/033464
PCT Pub. Date: Mar. 6, 2014

(65) Prior Publication Data
US 2015/0216707 A1    Aug. 6, 2015

(30) Foreign Application Priority Data

Aug. 31, 2012   (GB) .................................. 1215574.3

(51) Int. Cl.
*A61F 5/055* (2006.01)
(52) U.S. Cl.
CPC ..................... *A61F 5/055* (2013.01)
(58) Field of Classification Search
CPC ........ A61F 5/05; A61F 5/055; A61F 5/05883; A61F 5/05891; A61F 5/37; A61F 5/3707;
(Continued)

(56) References Cited

U.S. PATENT DOCUMENTS 1,523,884 A * 1/1925 Leduc ................ A41D 13/1115
                                                    128/863
2,562,121 A * 7/1951 Poux ........................ A61F 7/02
                                                    128/DIG. 23
(Continued)

FOREIGN PATENT DOCUMENTS

GB        2453996        4/2009

OTHER PUBLICATIONS

British Search Report dated Dec. 10, 2012 for corresponding Application No. GB1215574.3.
(Continued)

*Primary Examiner* — Keri J Nelson
*Assistant Examiner* — Adam Baker
(74) *Attorney, Agent, or Firm* — A.C. Entis-IP Ltd.; Kenichi N. Hartman; Allan C. Entis

(57) ABSTRACT

Cervical neck brace comprises an anterior brace element, and a posterior brace element which is engaged or engagable with the anterior brace element. The anterior brace element is positionable anteriorly on a user to extend across a cervical vertebral region, and the posterior brace element is positionable posteriorly on the user to extend across the cervical vertebral region. The posterior brace element is a sheet including a central support, an occipital support, and two activation arms, which are hingably connected to the central support. The posterior brace element has a first storage condition and a second in-use condition. A posterior cervical neck brace device and a method of supporting a vertebral region of a user are also provided.

17 Claims, 7 Drawing Sheets

(58) Field of Classification Search
CPC .... A61F 5/04; A61F 5/042; A61F 5/02; A61F 5/012; A61F 5/024; A61F 5/026; A61F 5/028; A61F 5/03; A61H 1/02; A61H 1/0218; Y10S 128/23; A41D 13/0512; A41D 13/11; A41D 13/1107; A41D 13/1138; B65D 5/06; B65D 5/18; B65D 3/06; A61M 16/06
USPC ............. 602/18, 17, 16, 12, 32, 36; 482/10; 224/575, 153–156, 181, 264; 220/6, 666; 229/404, 106; 128/863, 206.21
See application file for complete search history.

(56) References Cited

U.S. PATENT DOCUMENTS

| | | | |
|---|---|---|---|
| 3,957,040 | A | 5/1976 | Calabrese |
| 5,785,670 | A | 7/1998 | Hiebert |
| 5,797,713 | A | 8/1998 | Tweardy et al. |
| 5,904,662 | A * | 5/1999 | Myoga .................... A61F 5/055 602/18 |
| 6,045,523 | A * | 4/2000 | Donaldson .............. A61F 5/055 128/DIG. 23 |
| 6,308,345 | B1 * | 10/2001 | Williams, Jr. ..... A41D 13/0512 2/467 |
| 6,368,295 | B1 | 4/2002 | Lerman |
| 6,500,136 | B2 * | 12/2002 | Meyer ..................... A61F 5/055 602/17 |
| 6,733,469 | B2 | 5/2004 | Miyaji |
| 7,726,551 | B2 * | 6/2010 | Abbott .................... B65D 3/06 229/138 |
| 8,142,380 | B2 * | 3/2012 | Hasegawa ............... A61F 5/055 128/876 |
| 8,864,016 | B2 * | 10/2014 | Herman ................. B65D 1/265 229/128 |
| 9,737,161 | B1 * | 8/2017 | Li ...................... A47G 19/2205 |
| 2005/0102758 | A1 * | 5/2005 | Ramsbottom ........... A61F 5/055 5/636 |
| 2006/0130849 | A1 * | 6/2006 | Lieberman ............... A61F 5/03 128/845 |
| 2008/0201831 | A1 * | 8/2008 | Ronco ................ A41D 13/0153 2/468 |
| 2010/0185130 | A1 | 7/2010 | Patron Rizo |
| 2011/0066094 | A1 | 3/2011 | Thorgilsdottir et al. |

OTHER PUBLICATIONS

International Search Report dated Nov. 13, 2013 for corresponding Application No. PCT/GB2013/052277.

* cited by examiner

CERVICAL NECK BRACE

RELATED APPLICATIONS

The present application is a US National Phase of PCT Application No. PCT/GB2013/052277, filed on Aug. 29, 2013, which claims the benefit under 35 U.S.C. § 119(a)-(d) of British Application GB 1215574.3 filed on Aug. 31, 2012, the disclosures of which are incorporated herein by reference.

The present invention relates to a cervical neck brace, and more particularly but not necessarily exclusively to a posterior cervical neck brace device. Furthermore, the invention relates to a method of assembling such a cervical neck brace device, and to a method of supporting a vertebral region of a user, preferably using such a cervical neck brace.

In an event of an accident where an injured person is suspected of suffering head or neck injuries, one of the standard first aid steps is to immobilise the head and neck prior to moving the person to prevent further damage to that area. The torso too is very often immobilised to keep movement of the head and neck to a minimum during transfer of the injured person from the scene of the accident to an Accidence and Emergency department.

Immobilising the head and neck, and in particular the cervical vertebral region, of a person suspected of suffering head or neck injuries is important as damage to the head and neck can have serious consequences to other parts of the body. For example, injuries to the neck can lead to paralysis.

There are a wide variety of immobilisation devices available on the market, including different neck braces and head immobilisers. By way of example, refer to U.S. Pat. No. 6,368,295, U.S. Pat. No. 3,957,040, and U.S. Pat. No. 6,733,469.

The known cervical neck braces are at least in part preformed to an expected shape of the user. However, these assert pressure on the jugular vein, which may result in an increase in intracranial pressure, exacerbating a head injury.

Current cervical neck braces have a wrap-around design that places a patient's neck at risk of lateral rotation during application, which again is not preferable.

Furthermore, currently known cervical neck braces have a chin support which, when correctly fitted, restricts the opening of the patient's mouth. This may not be preferable, since the opening of the patient's mouth is required for actions such as intubation, x-raying and talking, and as such can cause extension of the cervical spine.

Furthermore, a head immobilising block may also be deemed advantageous to apply to the patient, in addition to the brace. The known braces are bulky and cumbersome, especially laterally of the patient, and this complicates fitment of a standard head immobilising block.

The present invention seeks to overcome these problems.

According to a first aspect of the invention, there is provided a cervical neck brace comprising an anterior brace element and a posterior brace element which is engaged or engagable with the anterior brace element, the anterior brace element positionable anteriorly on a user to extend in an inferior to superior direction across a cervical vertebral region, and the posterior brace element positionable posteriorly on a user to extend in an inferior to superior direction across the cervical vertebral region, the posterior brace element being a sheet including a central support, an occipital support which is hingably connected to the central support, and two activation arms which are hingably connected to the central support, the sheet having a first storage condition wherein the central support, occipital support and activation arms are coplanar or substantially coplanar, and a second in-use condition wherein, on hinging of the activation arms, the occipital support automatically folds relative to the central support.

Preferably, the activation arms, when in the second in-use condition, are interconnectable with the anterior brace element. Additionally or alternatively, first hinges which hingably connect the activation arms with the central support may be at least in part curved.

A second hinge which interconnects the occipital support with the central support may be at least in part curved. In this case, a radius of each first hinge of the activation arms is preferably less than a radius of the second hinge of the occipital support. Furthermore, the first and second hinges may intersect. In this case, the intersection preferably occurs at or adjacent to ends of the hinges.

Preferably, in the second in-use condition, the central support is non-planar. Additionally or alternatively, in the second in-use condition, the central support may be curved in at least two mutually perpendicular directions. Furthermore, in the second in-use condition, the central support is preferably dished. The occipital support may be curved.

Advantageously, in the second in-use condition, the occipital support may be non-planar. However, preferably, in the first storage condition, the posterior brace element is substantially flexible, and in the second in-use condition the posterior brace element is stiffened.

In the second in-use condition, the hinging of the activation arms may cause the central support to curve by which the occipital support folds. Furthermore, in the second in-use condition, the folding of the occipital support may be in the direction of a user-side concave surface of the central support.

The cervical neck brace preferably further comprises an at least in part recessable stiffening slot on the central support. In this case, the stiffening slot may be positioned substantially centrally on the central support, whereby a longitudinal axis extends in an inferior to superior direction. Additionally or alternatively, the stiffening slot preferably includes foldable longitudinal sides. Beneficially, hinges of the foldable longitudinal sides are preferably curved.

Preferably, the stiffening slot is dynamic, becoming at least in part recessed through curvature of the central support in the second in-use condition. The anterior brace element may additionally or alternatively include a forehead engagement element and a sternum engagement element interconnected with the forehead engagement element. In this case, the forehead engagement element and the sternum engagement element may be interconnected via telescopically adjustable struts.

The anterior brace element preferably further comprises a temple alignment indicator for guiding a positioning of the forehead engagement element and the sternum engagement element.

According to a second aspect of the invention, there is provided a posterior cervical neck brace device for location posteriorly on a user to extend in an inferior to superior direction across a cervical vertebral region, the device being a sheet and comprising: a central support, an occipital support which is hingably connected to the central support, and two activation arms which are hingably connected to the central support, the sheet having a first storage condition wherein the central support, occipital support and activation arms are coplanar or substantially coplanar, and a second in-use condition wherein, on hinging of the activation arms, the occipital support automatically folds relative to the central support.

According to a third aspect of the invention, there is provided a method of assembling a cervical neck brace according to the first aspect of the invention, the method comprising the steps of: a] activating a sheet-like planar or substantially planar posterior brace element to assume a non-planar configuration whereby an occipital support automatically folds relative to a central support; and b] engaging the activated posterior brace element with an anterior brace element, so as to form a supportive structure for a cervical vertebral region of a user.

According to a fourth aspect of the invention, there is provided a method of supporting a cervical vertebral region of a user, the method comprising the steps of: a] positioning an anterior brace element anteriorly on a user to extend in an inferior to superior direction across a cervical vertebral region; b] positioning a sheet-like planar or substantially planar posterior brace element posteriorly on a user to extend in an inferior to superior direction across the cervical vertebral region; c] activating the posterior brace element to form a non-planar configuration whereby an occipital support automatically folds towards the user for supporting an occipital region of the user's head; and d] engaging the anterior and posterior brace elements to form a rigid or substantially rigid supportive structure across the cervical vertebral region.

The invention will now be more particularly described, by way of example only, with reference to the accompanying drawings, in which.

Figure 1:
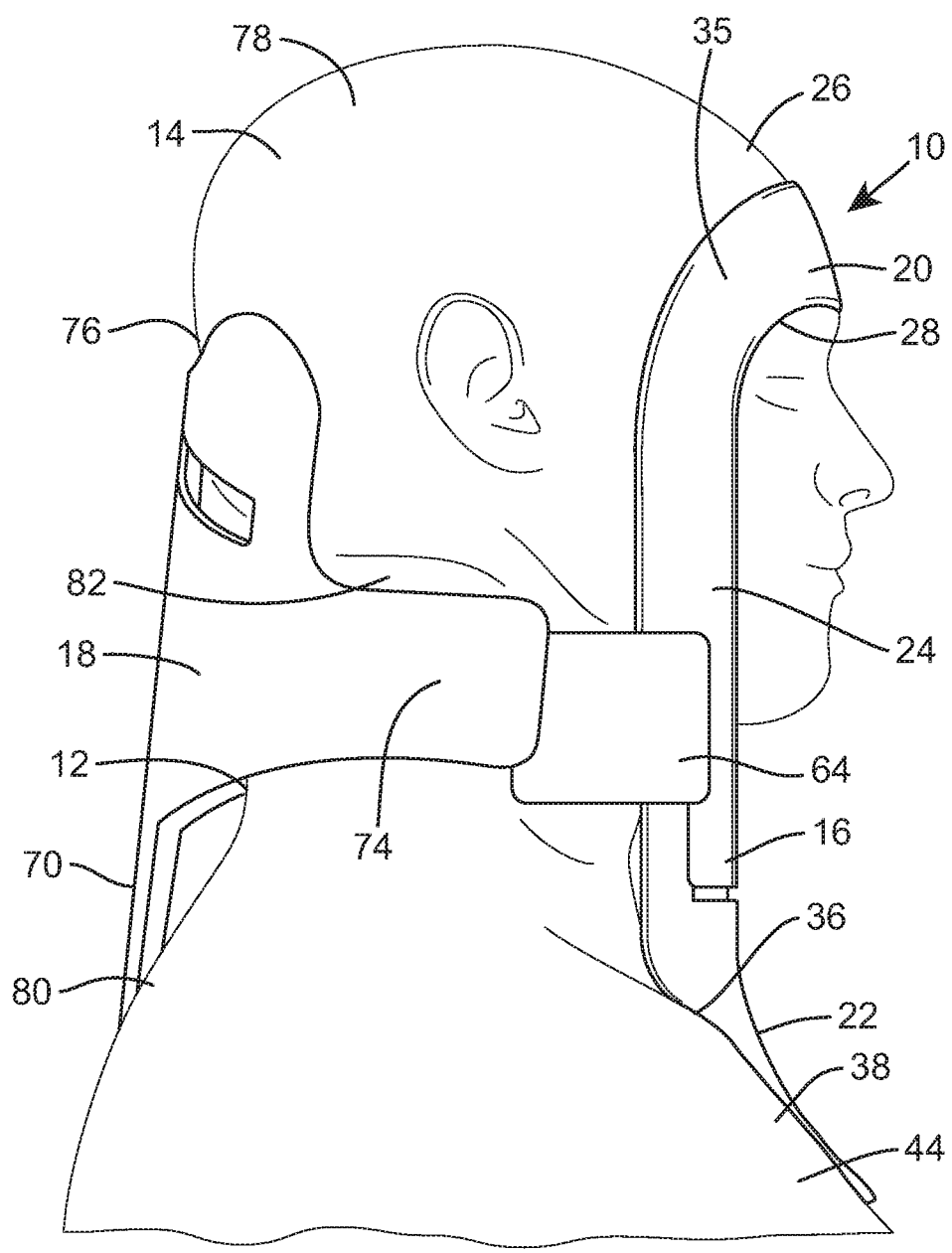
FIG. 1 is a side elevational view of a first embodiment of an in use cervical neck brace, in accordance with the first aspect of the invention and shown when applied to a patient.
Figure 2:
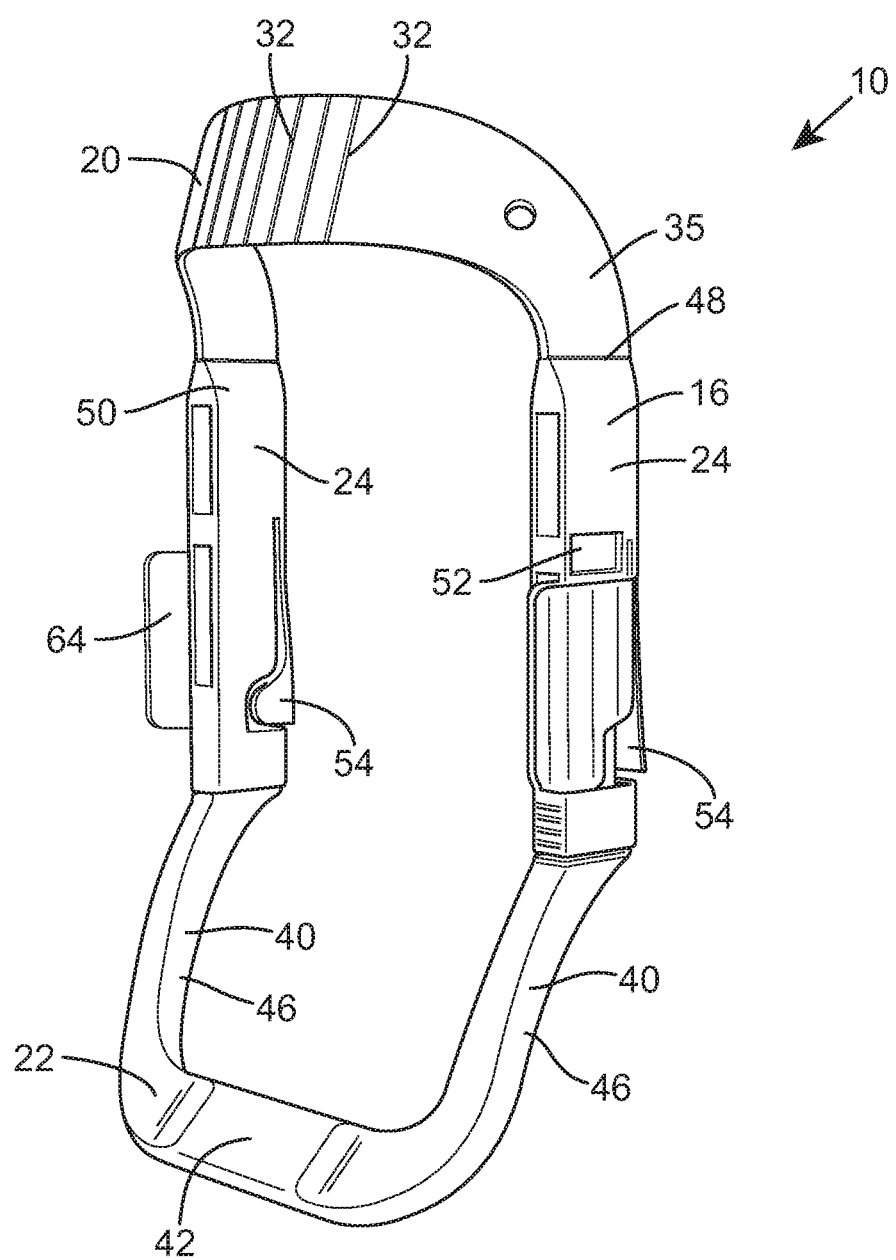
FIG. 2 is a front perspective view of one embodiment of an anterior brace element forming part of the cervical neck brace of FIG. 1.
Figure 3:
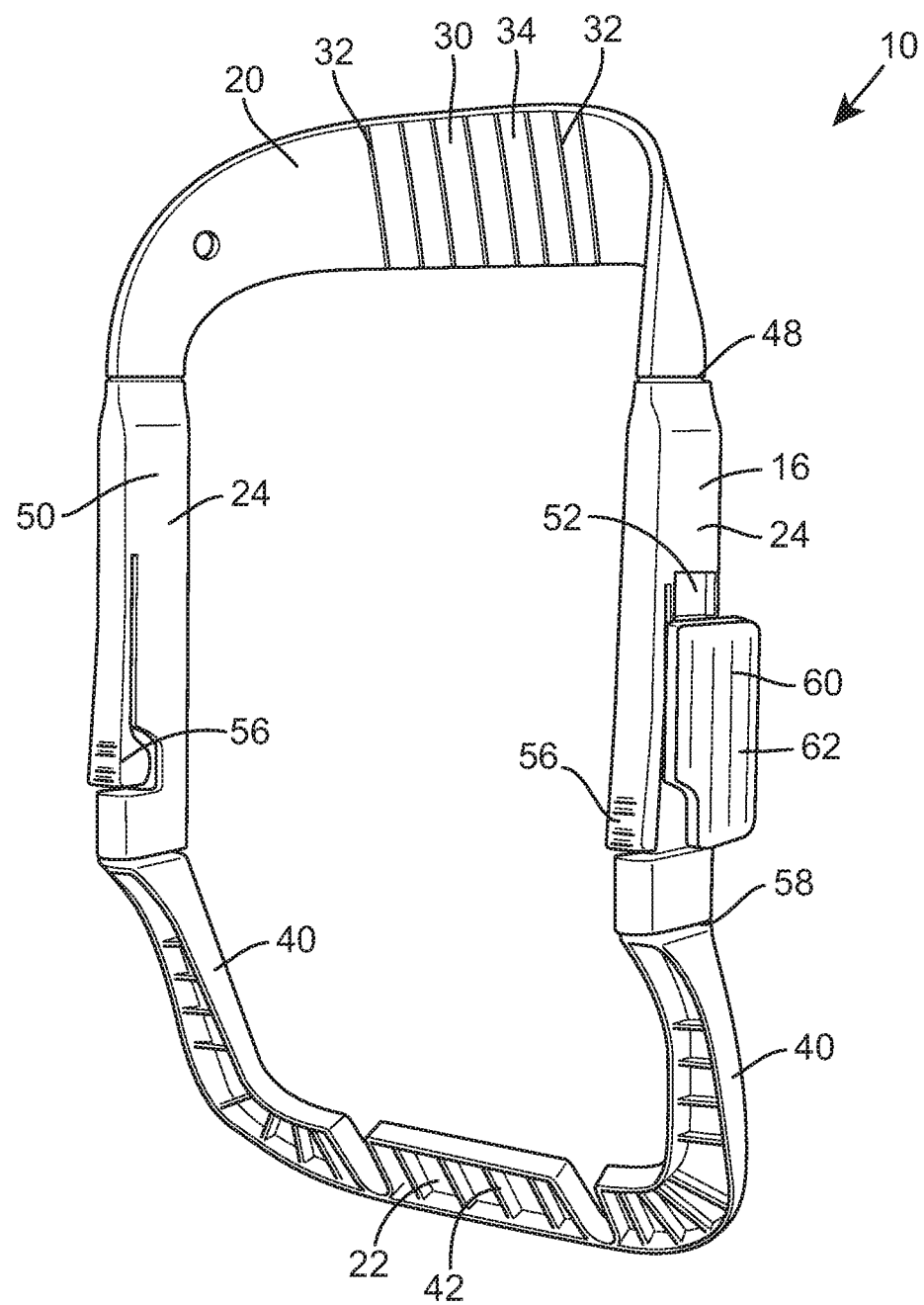
FIG. 3 is a rear perspective view of the anterior brace element.
Figure 4:
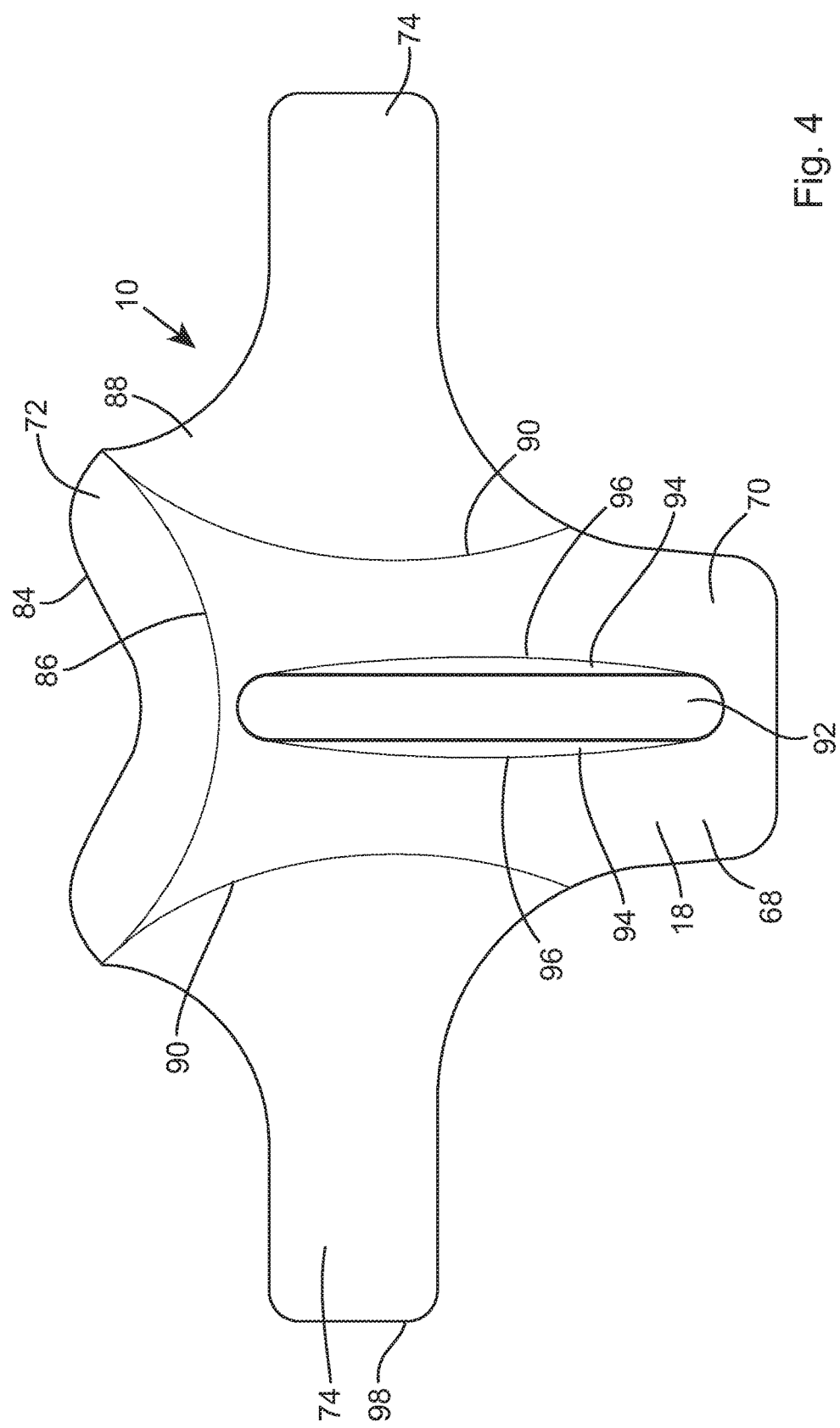
FIG. 4 is a plan view of a first embodiment of a sheet-like posterior brace element forming part of the cervical neck brace of FIG. 1 and shown in a first storage condition.
Figure 5A:
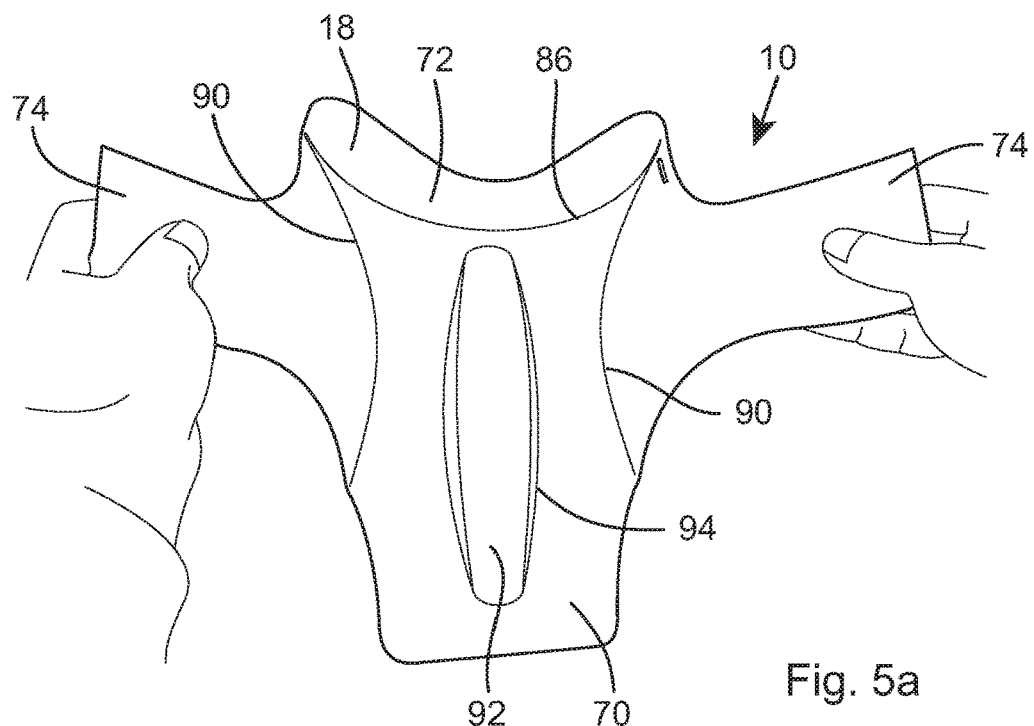
FIGS. 5a to 5e show the sheet-like posterior brace element of FIG. 2 being configured to adopt a second in-use condition.
Figure 5B:
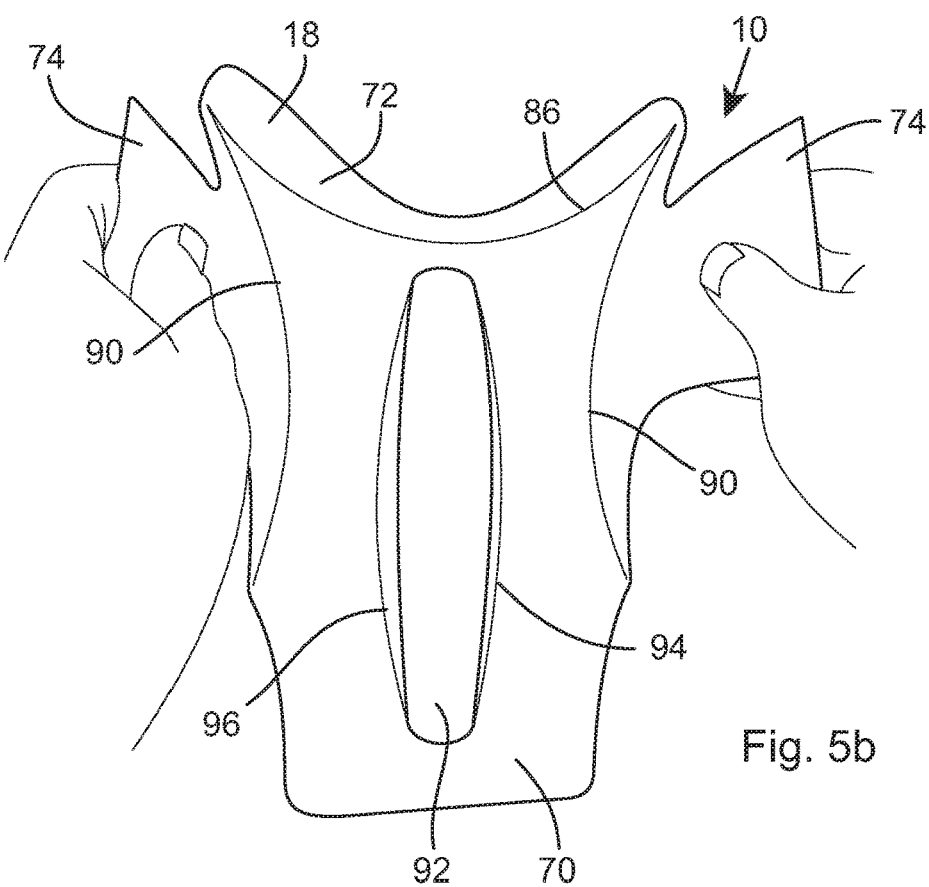
Figure 5C:
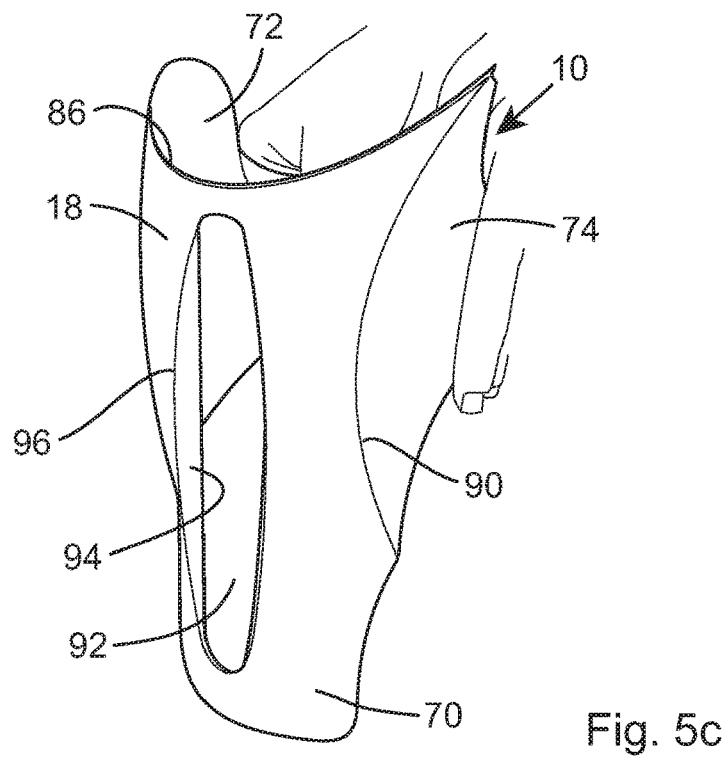
Figure 5D:
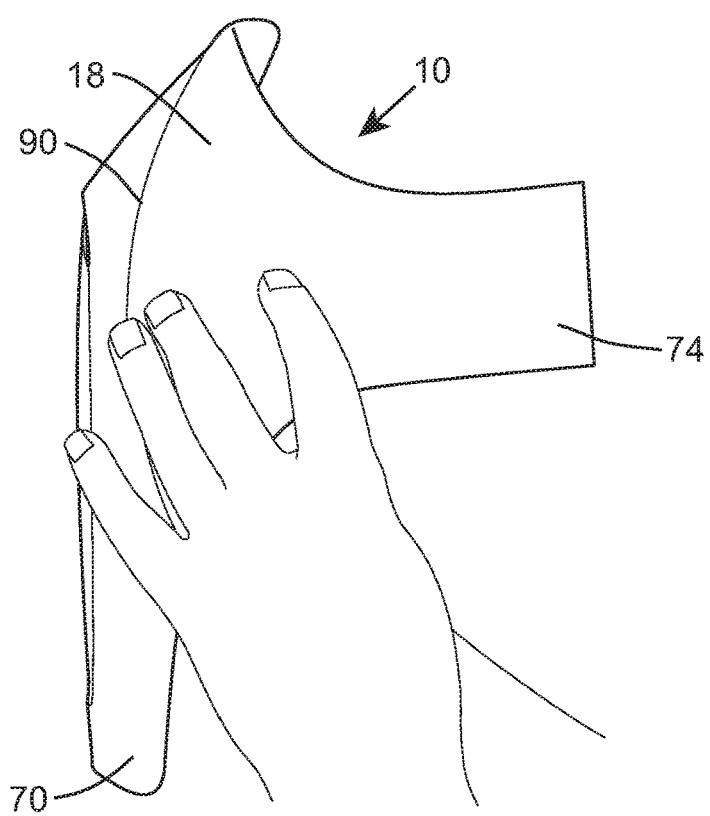
Figure 5E:
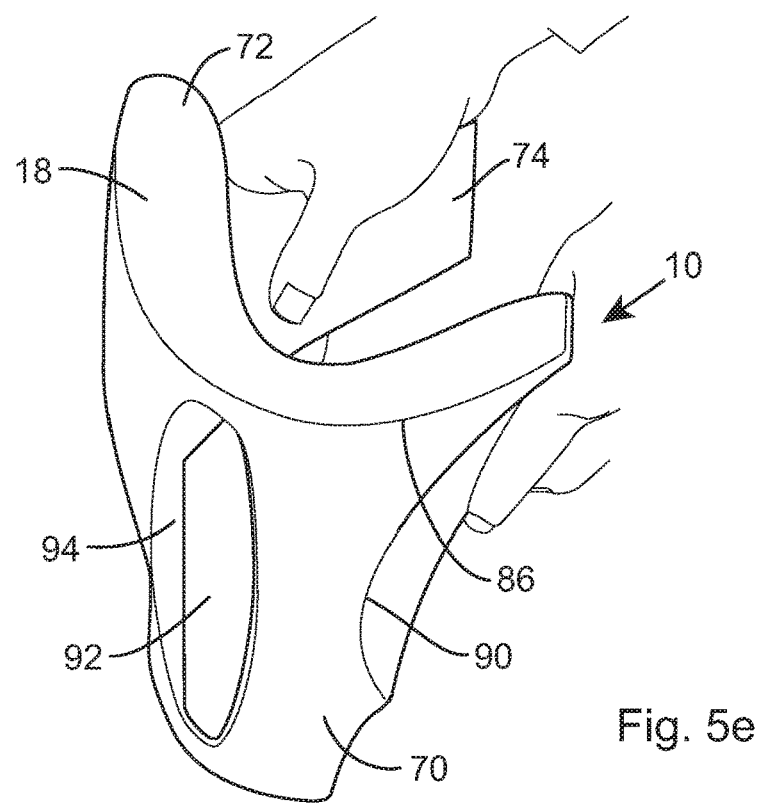

Referring firstly to FIGS. 1 to 4, there is shown a cervical neck brace 10 for supporting at least a cervical vertebral region 12 of a user 14. The cervical neck brace 10 comprises an anterior brace element 16 and a posterior brace element 18 which is, preferably releasably, engagable with the anterior brace element 16.

The anterior brace element 16 includes a forehead engagement element 20, a sternum engagement element 22, and two side strut elements 24 which interengage the forehead engagement and the sternum engagement elements 20, 22.

The forehead engagement element 20 is preferably rigid or substantially rigid and has a profiled arcuate longitudinal extent for complementarily or substantially complementarily receiving a user's forehead region 26 extending from the brow line 28.

Beneficially, the forehead engagement element 20 may be moulded plastics, and it may be overmoulded or include a layer of elastic padding material at least on a patient contact surface 30 for accommodating differently shaped heads.

Furthermore, the forehead engagement element 20 may include one or more, in this case being eight, laterally extending spaced-apart hinge portions 32. Preferably, the hinge portions 32 are positioned symmetrically about a central portion 34 of the forehead engagement element 20 and are spaced apart so as to be along the brow line 28, but terminate prior to the temple region 35.

The hinge portions 32 may be advantageously formed as living or live hinges, whereby the material of the forehead engagement element 20 has a reduced thickness to allow some minor longitudinal flex. Again, this is beneficial in allowing in situ dynamic profiling as the anterior brace element 16 is applied to the user 14.

The sternum engagement element 22 is also preferably rigid or substantially rigid, and has a profiled longitudinal extent which traverses a user's clavicles 36 and seats on a user's sternum 38, typically bridging the region of the sternoclavicular joint.

The sternum engagement element 22 comprises two arm members 40 and a cross-member 42 which interconnects the two arm members 40. Preferably being formed of moulded plastics, the two arm members 40 in this case are arcuately profiled along their longitudinal extents, preferably tapering to meet the ends of the cross-member 42. The cross-member 42 is also preferably moulded plastics, and it may be convenient to integrally form the sternum engagement element 22 therefore as one-piece.

A majority of a longitudinal extent of the cross-member 42 is rectilinear or straight, having curved ends to meet the two arm members 40. The cross-member 42 is planar or substantially planar at at least its central portion 34, but may be profiled to better match a user's sternum profiling.

The arcuate profiling of the arm members 40 enables the arm members 40 to extend laterally across the clavicles 36 whilst still being preferably at least in part supported thereby, before then meeting the cross-member 42 which extends across and is supportable by the sternum region 44 of the user 14. The arcuate profiling of the arm members 40 also forms grips 46 which aid a third party in grasping and manipulating the anterior brace element 16 during application to a user 14.

The side strut elements 24 are preferably at least substantially rigid in a lateral direction, and are preferably length-adjustable, such as by being telescopic. The side strut elements 24 extend linearly or substantially linearly from curved end portions of the forehead engagement element 20. A temple alignment indicator 48 is provided between the forehead engagement element 20 and the side strut element 24. The temple alignment indicator 48 may conveniently be a joint between the forehead engagement element 20 and the side strut element 24, or it may be a specifically formed dedicated marker, for example, if the forehead engagement element 20 and the side strut elements 24 are integrally formed together as one-piece.

The side strut elements 24 are again preferably moulded plastics, and comprise an outer receiving element 50, an inner strut 52 which is slidably received in the outer receiving element 50, and a detent 54 for releasably retaining the inner strut 52 in a set position relative to the outer receiving element 50. The detent 54 preferably has a manually operable catch 56, for example, as a sprung cantilevered arm, and this is preferably posteriorly facing so that it is less likely to be unintentionally released during use of the anterior brace element 16.

Furthermore, the manually operable catch 56 is preferably biased to a locked condition instead of an open condition, whereby release is possible only through manual activation.

Other detent or locking mechanisms can be envisaged, such as a ratchet mechanism or a pin and aperture mechanism. However, the detent 54 of the present invention is beneficial due to its ease of operation whilst the anterior brace element 16 is being applied.

A distal end 58 of the inner strut 52 of the side strut elements 24 is connected to an end of the sternum engagement element 22. By release of the detent 54, the sternum engagement element 22 can thus be linearly moved towards and away from the forehead engagement element 20 in order to best accommodate users of different sizes.

To engage the posterior brace element 18, a first part 60 of a releasable connector 62 is provided at each side strut element 24. In this case, the releasable connector 62 is a hook and loop fastening device, whereby the first part 60 of the releasable connector 62 is provided on a mounting plate 64 attached to a respective side strut element 24, and the second part is provided on the posterior brace element 18. Other fastening means can be considered, such as a snap-and-lock mechanism or a releasable ratchet mechanism. However, again, a hook-and-loop fastening device such as Velcro® enables quick and easy application and fastening together of the anterior and posterior brace elements 16, 18.

The posterior brace element 18 is formed from a sheet 68 of, preferably plastics, material such as polypropylene. The sheet 68 is preferably flat or substantially flat in a first storage condition, and comprises a central support 70, an occipital support 72, and two activation arms 74.

The central support 70 is longitudinally dimensioned to extend across or substantially in a superior to inferior direction across the cervical vertebral region 12 of the user 14, and typically between an occipital region 76 of a user's head 78 and towards a transverse part of the trapizius 80.

A lateral dimension of the central support 70 accommodates a typical lateral extent of a user's neck 82, and in this case is waisted at an intersection with the activation arms 74.

The occipital support 72 is hingably connected to an upper edge of the central support 70 along its proximal longitudinal edge. A free distal longitudinal edge 84 of the occipital support 72 is arcuately contoured to receive the occipital region 76 of the user's head 78.

An occipital hinge 86 which interconnects the occipital support 72 with the central support 70 is curved along at least a majority of, and in this case the entire, longitudinal extent, the reasons for which will become apparent hereinafter.

The activation arms 74 are elongate, having flared proximal ends 88 which intersect with side edges of the central support 70 at the waisted portion. The activation arms 74 are elongate and are adapted to meet the side strut elements 24 of the anterior brace element 16, when in use.

An arm hinge 90 which interconnects the activation arms 74 with the central support 70 is curved along at least a majority of, and in this case the entire, longitudinal extent. Furthermore, in this embodiment, the occipital hinge 86 and the arm hinges 90 intersect, and this intersection preferably occurs at or adjacent to the ends of the respective hinges.

The occipital hinge 86 and the arm hinges 90 are preferably living or live hinges, whereby the central support 70, occipital support 72, activation arms 74 and respective hinges can all be integrally formed together as one-piece. However, it is feasible that the various parts could be formed separately and interconnect via dedicated independent hinges.

A radius of the arm hinges 90 is preferably smaller than a radius of the occipital hinge 86. By way of example, a radius of the arm hinges may be in a range of 135 mm to 155 mm, and more preferably 148 mm. a radius of the occipital hinge 86 may be in a range of 160 mm to 180 mm, and more preferably 170 mm.

Through research and experimentation, it has been found that a larger occipital radius aids the automatic folding of the occipital support 72 over so that an included angle between the central support 70 and the occipital support 72 is in a range of 30 degrees to 60 degrees, and more preferably 45 degrees. This angle provides for occipital support 72, when in the in-use condition, being tangential or substantially tangential to an occipital region of a user's head. Such an angle also allows a thin layer of padding to be provided on the user interfacing surface, if required.

The posterior brace element 18 also includes an optional at least in part recessable stiffening slot 92 on the central support 70. In this case, the stiffening slot 92 is preferably positioned substantially centrally on the central support 70, so that a longitudinal axis extends in an inferior to superior direction of the central support 70.

The stiffening slot 92 may include foldable longitudinal sides 94. Hinges 96 of the foldable longitudinal sides 94 are curved, and are preferably living or live hinges so that the recessable slot 92 can be unitarily formed together with the central support 70.

The stiffening slot 92 may not be required, but it is advantageous for a carer to be able to have an access opening through the posterior brace element 18 to the posterior cervical vertebral region 12 of a user 14. To this end, by including foldable longitudinal sides 94, the stiffening slot 92 can improve the overall rigidity of the posterior brace element 18, when in use.

To engage the posterior brace element 18 with the anterior brace element 16, the second part 66 of the releasable connector 62 is provided at the distal end 98 of each activation arm 74, in this case on a user-facing surface.

In the first storage condition, the central support 70, occipital support 72 and the activation arms 74 of the sheet-like posterior brace element 18 are coplanar or substantially coplanar. The posterior brace element 18 may be flexible. In this condition, the posterior brace element 18 is slid posteriorly behind the user's neck 82 to extend in an inferior to superior direction across the cervical vertebral region 12.

As shown in FIGS. 5*a* to 5*e*, by then folding the activation arms 74 towards each other, due to the curved arm hinges 90, the central support 70 takes on a non-planar dished form which curves in at least two mutually perpendicular directions. Through the curvature of the central support 70, the longitudinal sides 94 of the stiffening slot 92 fold, whereby the stiffening slot 92 becomes at least in part recessed.

Furthermore, through the curvature of the central support 70, the occipital support 72 automatically folds in the direction of a user-side concave surface of the central support 70.

In this folded in-use condition, the central support 70, occipital support 72 and activation arms 74 are no longer coplanar. The occipital support 72 itself is non-planar and curved along at least its longitudinal extent, and more preferably curved in two mutually perpendicular directions, in other words laterally and longitudinally. Furthermore, the curvature of the central support 70 stiffens the posterior brace element 18, allowing the user's head 78 to be safely and securely supported by the folded occipital support 72.

With the posterior brace element 18 in position and folded to its in-use condition, the anterior brace element 16 is positioned anteriorly on the user 14 to extend in an inferior to superior direction across the cervical vertebral region 12.

The distal ends 98 of the activation arms 74 are connected to the anterior brace element 16 via the releasable connector 62, and the forehead engagement element 20 and the sternum engagement element 22 can be adjusted via the side strut elements 24 as necessary.

Figure 6:
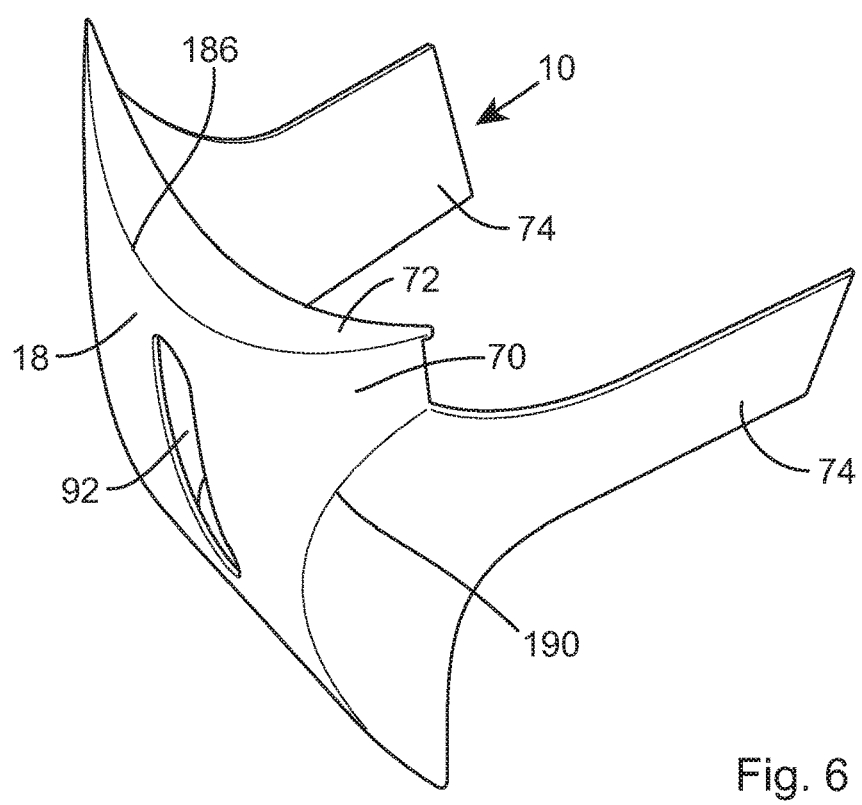
FIG. 6 shows a second embodiment of a sheet-like posterior brace element, shown in the second in-use condition.

Referring now to FIG. 6, a second embodiment of a posterior brace element 18 will now be described. In this embodiment, parts which are similar or identical to those of the first embodiment use the same references, and therefore further detailed description is omitted.

The posterior brace element 18 is again formed from a sheet 68 of, preferably plastics, material. The sheet 68 is preferably flat or substantially flat and flexible in a first storage condition, and as in the first embodiment stiffened when activated in a second in-use condition.

As with the first embodiment, the posterior brace element 18 comprises a central support 70, an occipital support 72 which is hingably connected to the central support 70, and two activation arms 74 which are hingably connected to the central support 70. However, the occipital hinge 186 and the arm hinges 190 are spaced apart, and in this case preferably in the range of 5 mm to 10 mm. This allows the central support 70 to be extended longitudinally, for example, for larger users, or allows the dimensions of the flared proximal portions of the activation arms 74 to be altered. Furthermore, it also allows the curvature of the central support 70 to be altered, again enabling alteration of the stiffening characteristics.

Although two embodiments of the posterior brace element have been described above, any suitable arrangement of a posterior cervical neck brace device can be utilised providing the occipital support is automatically foldable via the activation arms.

Although both activation arms are preferably initially separate of the anterior support element, one of the activation arms could be initially engaged with one side of the anterior support element prior application of the cervical neck brace to a patient.

Furthermore, although the arm hinges and the occipital hinge are curved along their entire longitudinal extents, it is feasible that at least a portion of the arm hinges may be straight or substantially straight. For example, a bottom portion of at least one arm hinge and preferably both arm hinges could be straight, whereby the curvature at the top adjacent the occipital support would still allow the automatic folding of the occipital support.

It is preferred that the occipital hinge is curved along its entire longitudinal extent, but it may include a straight portion, for example, partway and preferably midway therealong, as necessity dictates.

It is thus possible to provide a cervical neck brace having an anterior brace element and an initially sheet-like posterior brace element, wherein the posterior brace element provides an automatically foldable occipital support. This therefore enables simplified positioning of the posterior brace element posteriorly of a user across the cervical vertebral region, whilst allowing remote activation of the occipital support thereby dispensing with the need for a carer to manually access the posterior cervical vertebral region and occipital region.

The embodiments described above are provided by way of examples only, and various modifications will be apparent to persons skilled in the field without departing from the scope of the invention as defined by the appended claims.

The invention claimed is:

1. A cervical neck brace comprising an anterior brace element and a posterior brace element which is engaged or engagable with the anterior brace element, the anterior brace element being positionable anteriorly on a user to extend in an inferior to superior direction across a cervical vertebral region and including a forehead engagement element and a sternum engagement element interconnected with the forehead engagement element, and the posterior brace element being positionable posteriorly on a user to extend in an inferior to superior direction across the cervical vertebral region, wherein, the posterior brace element comprises a central support, an occipital support hingably connected to the central support by a first hinge that is curved at least in part, and two activation arms, each activation arm being hingably connected to the central support, respectively, by a second hinge that is curved at least in part;

the posterior brace element is configured to have a first storage condition wherein the central support, occipital support and activation arms are coplanar or substantially coplanar;

the respective curvatures of the first and second hinges are configured such that folding the activation arms along the respective second hinges causes the central support to transition from a planar conformation to a curved conformation and causes the occipital support to automatically fold relative to the central support along the first hinge, to achieve a second in-use condition of the posterior brace element; and the central support, the occipital support, the activation arms, and the first and second hinges are integrally formed together as one-piece.

2. A cervical neck brace as claimed in claim 1, wherein the activation arms, when in the second in-use condition, are interconnectable with the anterior brace element.

3. A cervical neck brace as claimed in claim 1, wherein a radius of each of the second hinges connecting the activation arms to the central support is less than a radius of the first hinge connecting the occipital support to the central support.

4. A cervical neck brace as claimed in claim 1, wherein the first hinge and the second hinges intersect.

5. A cervical neck brace as claimed in claim 4, wherein the intersection occurs at or adjacent to ends of the first hinge and the second hinges.

6. A cervical neck brace as claimed in claim 1, wherein, in the first storage condition, the posterior brace element is flexible, and in the second in-use condition the posterior brace element is stiffened.

7. A cervical neck brace as claimed in claim 1, wherein, in the second in-use condition, the hinging of the activation arms causes the central support to curve by which the occipital support folds.

8. A cervical neck brace as claimed in claim 1, wherein, in the second in-use condition, the folding of the occipital support is in the direction of a user-side concave surface of the central support.

9. A cervical neck brace as claimed in claim 1, further comprising an at least in part recessable stiffening slot on the central support.

10. A cervical neck brace as claimed in claim 9, wherein the stiffening slot is positioned substantially centrally on the central support, whereby a longitudinal axis extends in an inferior to superior direction.

11. A cervical neck brace as claimed in claim 9, wherein the stiffening slot includes foldable longitudinal sides.

12. A cervical neck brace as claimed in claim 11, wherein hinges of the foldable longitudinal sides are curved.

13. A cervical neck brace as claimed in claim 9, wherein the stiffening slot is dynamic, becoming at least in part recessed through curvature of the central support in the second in-use condition.

14. A cervical neck brace as claimed in claim 1, wherein the forehead engagement element and the sternum engagement element are interconnected via telescopically adjustable struts.

15. A cervical neck brace as claimed in claim 1, wherein the anterior brace element further comprises a temple alignment indicator.

16. A posterior cervical neck brace device for location posteriorly on a user to extend in an inferior to superior direction across a cervical vertebral region, the device comprising: a central support; an occipital support hingably connected to the central support by a first hinge that is curved at least in part; and two activation arms, each activation arm being hingably connected to the central support, respectively, by a second hinge that is curved at least in part,
- the device having a first storage condition wherein the central support, occipital support and activation arms are coplanar or substantially coplanar,
- the respective curvatures of the first and second hinges being configured such that folding the activation arms along the respective second hinges causes the central support to transition from a planar conformation to a curved conformation and causes the occipital support to automatically fold relative to the central support along the first hinge, to achieve a second in-use condition of the device, and
- the central support, the occipital support, the activation arms, and the first and second hinges being integrally formed together as one-piece.

17. A method of supporting a cervical vertebral region of a user, the method comprising the steps of: a] positioning an anterior brace element anteriorly on a user to extend in an inferior to superior direction across a cervical vertebral region; b] positioning a planar or substantially planar posterior brace element posteriorly on a user to extend in an inferior to superior direction across the cervical vertebral region, the posterior brace element comprising a central support, an occipital support hingably connected to the central support by a first hinge that is curved at least in part, and two activation arms, each activation arm being hingably connected to the central support, respectively, by a second hinge that is curved at least in part, the device having a first storage condition wherein the central support, occipital support and activation arms are coplanar or substantially coplanar, and the respective curvatures of the first and second hinges are configured such that folding the activation arms along the respective second hinges causes the central support to transition from a planar conformation to a curved conformation and causes the occipital support to automatically fold relative to the central support along the first hinge, to achieve a second in-use condition of the device, and the first and second hinges being integrally formed together as one-piece; c] activating the posterior brace element to form a non-planar configuration whereby the occipital support automatically folds towards the user for supporting an occipital region of the user's head; and d] engaging the anterior and posterior brace elements to form a rigid or substantially rigid supportive structure across the cervical vertebral region.

\* \* \* \* \*